United States Patent
Zuber et al.

(10) Patent No.: US 7,329,774 B2
(45) Date of Patent: Feb. 12, 2008

(54) METHOD AND PLANT FOR THE MANUFACTURE OF CARBOXYLIC ACID ESTER BY MEANS OF A REACTIVE DISTILLATION

(75) Inventors: Laurent Zuber, Winterthur (CH); Oliver Bailer, Winterthur (CH); Stefan Sander, Winterthur (CH); Heinz Meierhofer, Rickenbach (CH)

(73) Assignee: Sulzer Chemtech AG, Winterthur (CH)

( * ) Notice: Subject to any disclaimer, the term of this patent is extended or adjusted under 35 U.S.C. 154(b) by 5 days.

(21) Appl. No.: 11/348,926

(22) Filed: Feb. 7, 2006

(65) Prior Publication Data
US 2006/0178524 A1 Aug. 10, 2006

(30) Foreign Application Priority Data
Feb. 10, 2005 (EP) .................. 05405063

(51) Int. Cl.
*C07C 69/02* (2006.01)

(52) U.S. Cl. .................................. 560/231

(58) Field of Classification Search .............. None
See application file for complete search history.

(56) References Cited

U.S. PATENT DOCUMENTS

| 6,028,215 | A  | * | 2/2000  | Bessling et al. | ............ | 560/265 |
| 6,458,992 | B1 | * | 10/2002 | Lederer et al.  | ............. | 560/239 |
| 6,573,400 | B1 | * | 6/2003  | Bottcher et al. | ............. | 560/174 |
| 7,091,367 | B2 | * | 8/2006  | Moritz et al.   | ............... | 554/170 |
| 7,160,524 | B2 | * | 1/2007  | Lederer et al.  | ............. | 422/191 |

FOREIGN PATENT DOCUMENTS

| DE | 19829809 A1 | 1/1999 |
| EP | 1424115 A1  | 6/2004 |
| WO | WO 99/48855 A | 9/1999 |

* cited by examiner

*Primary Examiner*—Yvonne Eyler
*Assistant Examiner*—M. Louisa Lao
(74) *Attorney, Agent, or Firm*—Francis C. Hand; Carella, Byrne, Bain, et al.

(57) ABSTRACT

Carboxylic acid ester is produced by esterification of carboxylic acid and an alcohol in a catalytic reaction zone of a first column at a pressure not greater than ambient pressure. The resultant sump product is distilled in a reaction zone of a second column at a pressure greater than 1.5 bar to obtain a second liquid sump product containing carboxylic acid ester with an carboxylic acid content of less than 100 ppm by weight at a lower end of the column. Neutralization of the second liquid sump product with a base is not required.

10 Claims, 2 Drawing Sheets

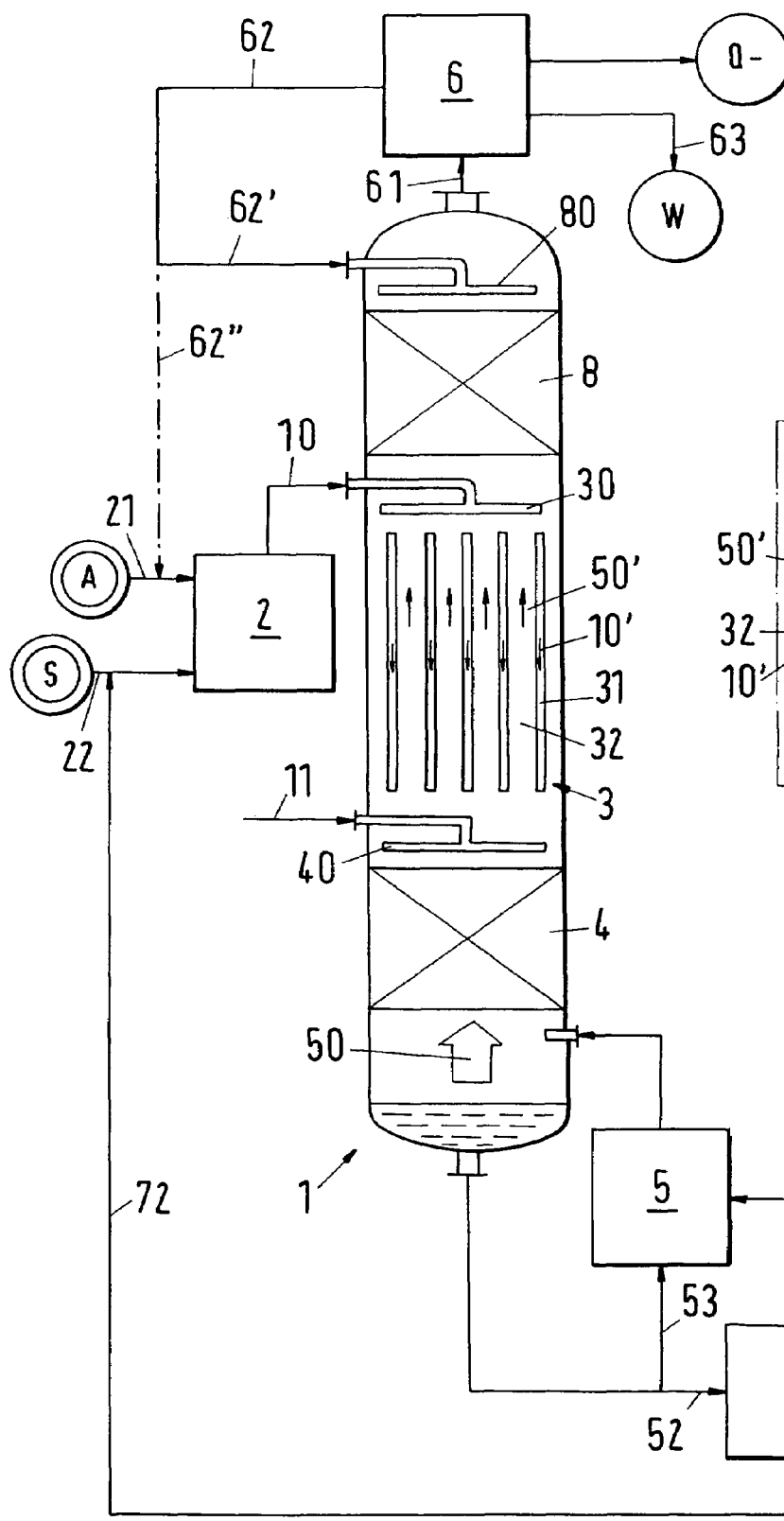
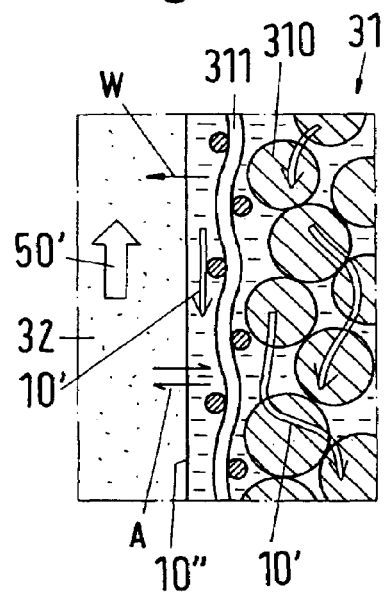

METHOD AND PLANT FOR THE MANUFACTURE OF CARBOXYLIC ACID ESTER BY MEANS OF A REACTIVE DISTILLATION

This invention relates to a process for the manufacture of carboxylic acid ester by means of a reactive distillation and plant. More particularly, this invention relates to a process for the manufacture of butyl acetate or isobutyl acetate, by means of an esterification of acetic acid with butanol or isobutanol.

As is known from WO-A 99 4855, (corresponding to U.S. Pat. No. 6,458,992), reactive distillation has been used in an esterification process for the production of carboxylic acid ester. In this process, the carboxylic acid ester has to boil at a higher temperature than the educts carboxylic acid and alcohol. For example, the process performs a reactive distillation in a column that employs a solid material catalyst and wherein an esterification and a distillative separation are carried out in three zones, i.e. a reaction zone, an upper separating zone and a lower separating zone. In addition, a head product and a sump product are produced. The head product is then separated into an aqueous phase and an organic phase while a residue of carboxylic acid and alcohol are removed from the sump product to obtain the carboxylic acid ester. The heat that is required to drive the reactive distillation is supplied at a temperature for which a pressure not greater than the ambient pressure is set in the evaporated sump product.

Butyl acetate or isobutyl acetate can obtained as a higher boiling sump product in a column in which the esterification of acetic acid is carried out catalytically with n-butanol or isobutanol by reactive distillation, with this catalysis taking place in a reaction zone between two separating zones.

In the following, the alcohol butanol (BuOH) will also be understood to mean isobutanol or a further alcohol (A) and correspondingly the ester butyl acetate (BuOAc) will be understood to mean isobutylacetate or a further ester (E).

The organic portion (BuOH+BuOAc or A+E) that is separated from the head product of the column is returned into the upper separating zone. Because of the separating zones in the column, virtually no acetic acid (S) appears either in the sump product or in the head product. Acetic acid which escapes out of the reaction zone up-wards and down-wards is transported back into the reaction zone due to the two separating zones, where the acetic acid is ultimately completely or at least almost completely converted. Acetic acid and unwanted byproducts appear only in small amounts as pollutants in butyl acetate. Acetic acid hydride ($CH_3$—$CO)_2O$ (or a mixture) can be used instead of acetic acid ($CH_3COON$) as an educt. With water, acetic acid hydride converts to acetic acid—which occurs during esterification.

It has also been known to achieve an improvement in the quality of the product (butyl acetate) with respect to the embodiments of the method described in WO-A 99 48855, (corresponding to U.S. Pat. No. 6,458,992), being able to reduce the pollution of the butyl acetate by the undesired byproducts (dibutylether) through the use of special solid catalysts. However, this improvement leads to an increase in the proportion of acetic acid in the product. The reason for this is seemingly that the newly used solid catalysts are only stable at temperatures which are lower than in the described examples of the already known process and, for this reason, the reactive distillation has to be carried out correspondingly at a lower temperature and, consequently, at a lower pressure—i.e. in vacuum operation.

The acetic acid that is removed from the sump product in a part of the plant following the reactive distillation is neutralized with a base In accordance with a previously known method for the manufacture of butyl acetate, in which a liquid catalyst Is used in place of the solid catalyst (see WO-A 99 48856, (corresponding to U.S. Pat. No. 6,458,592), where the older prior art is appraised). The salts formed during neutralization with the base are removed from the butyl acetate by a wash and by a phase separation. The disadvantage of this method is that a special base has to be made available and that a disposal of the separated salts which would heavily pollute the environment is expensive. It would therefore be advantageous to be able to manage without such neutralization.

Accordingly, it is an object of the invention to provide an improved process for the manufacture of carboxylic acid ester.

It is another object of the invention to remove the carboxylic acid, in particular, acetic acid, which is contained in the carboxylic ester (butyl acetate) produced by means of a reactive distillation without the step of neutralization using a base.

Briefly, the invention provides a process for the manufacture of carboxylic acid ester comprising the steps of supplying alcohol and carboxylic acid to a catalytic reaction zone of a first column for esterification therein at a pressure not greater than ambient pressure to obtain a first vaporous head product at an upper end of the first column and a first liquid sump product at a lower end of the first column; of supplying heat to the lower end of the first column to effect esterification; of distilling the first liquid sump product in a reaction zone of a second column filled with material exchange means at a pressure greater than 1.5 bar to obtain a second vaporous head product containing carboxylic acid at an upper end of the second column and a second liquid sump product containing carboxylic acid ester at a lower end of the second column and of supplying heat to the second liquid sump product at a pressure greater than 1.5 bar.

In accordance with the process, the second liquid sump product is removed with a carboxylic acid content of less than 100 ppm by weight.

The process for the manufacture of carboxylic acid ester by an esterification is carried out in the first column by means of a reactive distillation, for example, as described in copending U.S. Pat. No. 7,091,387. The carboxylic acid ester boils at a higher temperature than the educts earboxylic acid and alcohol.

In the esterification, a solid material catalyst is used. The esterfication and a distillative separation take place in three zones, namely in the reaction zone, in an upper separating zone and also in a lower separating zone.

The first head product is separated into an aqueous phase and an organic phase with the organic phase being recycled to the first column.

The heat which is required to drive the reactive distillation is supplied at a temperature for which a pressure not greater than the ambient pressure is set in the evaporated sump product.

The removal of carboxylic acid and alcohol from the first sump product is carried out by distillation in the second column. In this arrangement, heat is supplied to the second sump product, that largely consists of carboxylic acid ester and small quantities of further materials, at a temperature for which a pressure greater than the ambient pressure is set in the evaporated sump product.

In the analysis of the task to provide an improved process, it was initially assumed that the proportion of acetic acid can be reduced in the first sump product by increasing the number of the theoretical separating stages in the lower separating zone. It is to be assumed from experience that the separating effects are better with vacuum conditions than at ambient pressure. It was also known that with increasing pressure, the relative volatility of the components in a mixture is reduced so that the mixture is more difficult to separate at increased pressure. The process of first choice, to make the separation of a mixture by distillation easier, is to carry out the separating process at lower pressure, in particular in a vacuum rather than at ambient pressure. With these considerations in mind one decided to investigate whether a distillation at lower pressure actually resulted in the desired separating effect. On the basis of existing operating data, one had to conclude that the separation is not better under these conditions. Contrary to generally recognized experience, it was decided to analyse the separation experimentally at higher pressures.

Surprisingly, results were obtained which did not correspond to the rules of experience: the separation was better at increased pressure. This result led to the distillation being carried out in a second column and at an increased pressure.

The invention also provides a plant for the manufacture of carboxylic acid ester comprising a pre-reactor for performing a first stage of esterification of an alcohol and a carboxylic acid without material separation; a first column having a catalytic reaction zone connected to the pre-reactor to receive and distill the esterified alcohol and carboxylic acid into a first vaporous head product at an upper end of the first column and a first liquid sump product at a lower end of the first column; and a second column connected to the first column to receive and separate the first sump product into a second vaporous head product containing carboxylic acid at an upper end of the second column and a second liquid sump product containing carboxylic acid ester at a lower end of the second column.

The plant also has a first return line connecting an outlet of the second column to the pre-reactor to deliver the second head product thereto; an apparatus for liquefying the first vaporous head product and for separating the liquefied first head product into an organic phase and water; and a return line connecting the apparatus to the pre-reactor to recycle the organic phase to the pre-reactor.

As an option, the plant may also have a neutralization stage connected to an outlet of the second column to receive the carboxylic acid ester and a base to form a salt of the base and residual acetic acid in the carboxylic acid ester as well as a means for washing and phase separating the formed salt from the carboxylic acid ester.

These and other objects and advantages will become more apparent from the following detailed description taken in conjunction with the drawings wherein:

FIG. 1 illustrates a plant with two columns which are used in the carrying out of the process in accordance with the invention;

FIG. 2 illustrates a section from a catalytic reaction zone in the first column of the plant of FIG. 1;

Figure 4:
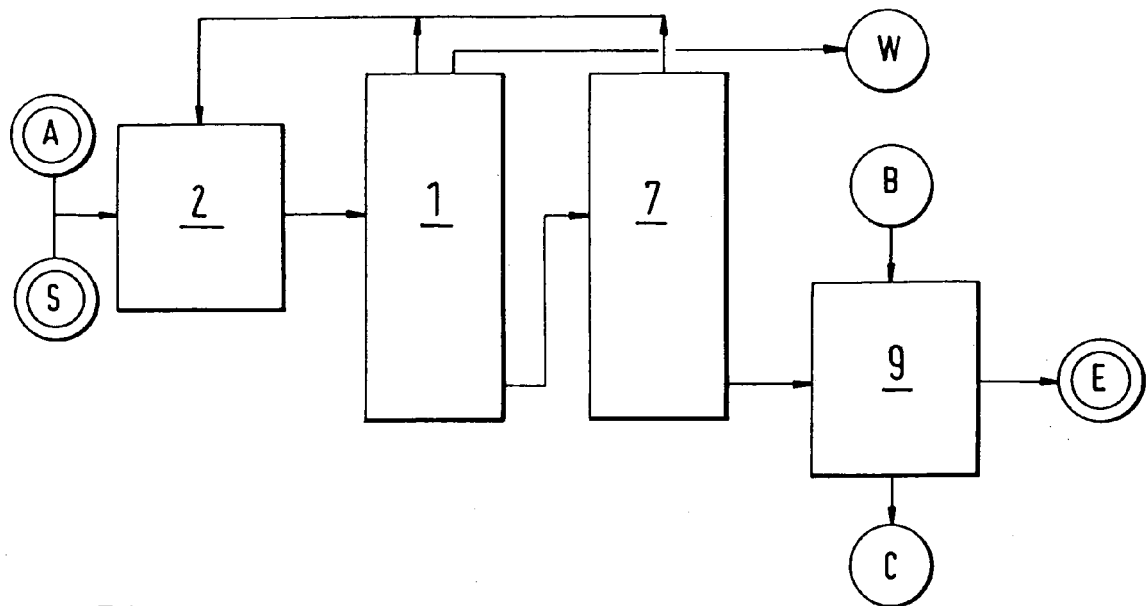
FIG. 4 illustrates a block diagram of a special complete plant in which a process in accordance with the invention is used.

Referring to FIG. 1, the plant is operated for the manufacture of carboxylic acid esters, and particularly, butylacetate. As illustrated, the plant includes a first column 1 in which an esterification is carried out by reactive distillation and butylacetate containing acetic acid is extracted from the sump of the column 1. This product, the quality of which is still insufficient, is supplied through a line 52 to a plant part 7 for cleaning.

The feed products for the process in accordance with the invention are butanol, hereinafter referred to as alcohol A, and acetic acid S each of which is separately supplied via respective lines 21,22 to a prereactor 2.

The sump product of the first column 1, hereinafter referred to as first sump product, is treated further in the plant part 7 using a second column 70 (see FIG. 3) so that ultimately a butylacetate ester (E) can be obtained, the acetic acid content of which is below 100 ppm by weight. The cleaned product is removed from the column 70 through a line 71. A head product separated in the second column 70, namely the second head product, is returned via a line 72 into the reactive distillation process.

Referring to FIG. 1, the acetic acid (S) and the alcohol A are supplied via the lines 21,22, prereactor 2 and a line 10 to the first column 1 in a molar ratio in the range between 5:1 and 1:10, preferably with an excess of alcohol A which does not exceed 100% (molar ratio 1:2). These feed products can be supplied separately to the column 1 or in a mixture having been mixed in the prereactor 2.

The column 1 contains a packing part which forms a reaction zone 3 and in which the esterification is carried out by means of a heterogeneous catalysis. Alcohol A and acetic acid S (together with a product mixture which is possibly created in the pre-reactor 2 or brought into it by return and partially reacted) are applied onto the packing of the reaction zone 3 through the line 10 using a distributor 30 in a conventional manner.

A lower separating zone 4, containing a distributor 40 and a second packing, is arranged below this packing of the reaction zone 3. A line 11 through which additional alcohol A can be supplied and the distributor 40 are optional. The inserts consisting of the reaction zone 3 and the lower separating zone 4 act as a stripping part.

Heat Q+ is required to drive the reactive distillation and is supplied to a branch stream 53 from the line 52 in an apparatus 5. The supplied heat Q+ generates a vapor flow 50 in the sump of the column 1, which vapor flow 50 contains alcohol A, acetic acid S and a small proportion of butylacetate. This vapor flow 50 forms a counterflow to a trickle film flowing on the packing and on the one hand returns acetic acid to the reaction zone. On the other hand, a vapor flow 50' is formed that acts as a stripping gas with which water W is removed from the reaction zone 3, whereby the reaction kinetics are influenced to the benefit of the ester formation.

The heat Q+ required for the vaporization In the lower separating zone 4, water W and, moreover, alcohol A are already taken up from the liquid mixture by the vapor stream 50' which passes through the reaction zone 3.

An upper separating zone 8 containing a further packing and a distributor 80 are installed in the first column 1 above the reaction zone 3. Acetic acid S which is carried along by the vapor flow 50 is intercepted by the upper separating zone 8. A trickle film flowing on the packing in the separating zone 8 transports the intercepted acetic acid back into the reaction zone 3.

A vapor flow emerges from the head of the column 1 via a line 61 as the first head product and is liquefied and separated in an apparatus 6 into two fractions 62 and 63, for example by means of decanting, while heat Q− is expelled. The fraction 63 is substantially liquid water W, in which residual organic portions are dissolved. The other fraction 62 is a liquid organic phase that is returned as reflux 62' onto the upper separating zone 8 via the distributor 80.

The organic phase 62 from the first head product is returned directly (reflux 62') or indirectly (connection 62" shown as a dotted line) into the reaction zone 3. Values between 5:1 to 1:20 are selected for the mass ratio between the freshly supplied alcohol (via line 21) and the returned organic phase 62. Typically, 60% to 100% of the total amount of separated organic phase 62 is used for the reflux 62'.

In the example shown, the catalytic reaction zone 3 is composed of vertical layers 31 between which flow passages 32 lie for the vapor flow 50' that serves as a stripping gas. A mixture 10', which contains the feed materials A and S, lies in and on the layers 31. Details as regards the reaction zone 3 are illustrated in the cutout of FIG. 2, where a border region of the layer 31 is shown. This border region includes parts of a flow passage 32 with the vapor flow 50' and also the layer 31 which contains a granulate 310 of a catalyst. A fabric 311 of a durable material forms a container in which the granulate 310 is contained. The mixture 10' flows inside the container and on the outside of the fabric 311 with meandering flow filaments inside the container and as a trickle film 10" outside the container. As a result of the free surface of the trickle film 10", water W passes into the vapor flow 50' because there is a relatively low partial pressure of the water present in this. The partial pressure of the alcohol A is relatively high so that there is largely an equilibrium for the giving up and taking up of molecules of the alcohol A at the surface of the trickle film 10".

The reactive distillation is carried out using column inserts on which or in which the catalyst is fixed and through which a good contact is made possible, both between the liquid phase and the catalyst, and also between the liquid phase and the gaseous phase. The column inserts serving as a support structure for the catalyst are formed using shapes known per se. These column inserts can also combine different shapes, namely a combination of at least one distillation base and/or at least one structured packing element, which is made up of zigzag layers or corrugated layers forming a crossed channel structure and/or at least one zone of bulk filled bodies. Suitable kinds of packing for the reaction zone 3 are described in EP-A-0 396 650 or in EP-A-0 631 813. Other known reactive distillation apparatus can be used for this purpose, among other things also bases with special devices (see U.S. Pat. No. 5,914,011).

An ion exchange resin can be used as a catalyst, and is preferably present in a strongly acid form and is macroporous. The catalyst has to be usable at temperatures between 80° C. and 120° C.; the catalyst can only lose activity moderately in this temperature range.

The feed materials alcohol A and acetic acid S are advantageously already brought to reaction in the pre-reactor 2 up to an equilibrium state in which 10% to 75% of the acetic acid S is converted into Ester E. Thus, a mixture of alcohol A, acetic acid 5, ester E and water W enters the first column 1. Then, the remaining acetic acid S is converted further in the reaction zone 3 so that a total conversion of over 95% of the acetic acid fed into the prereactor 2 is achieved.

Figure 3:
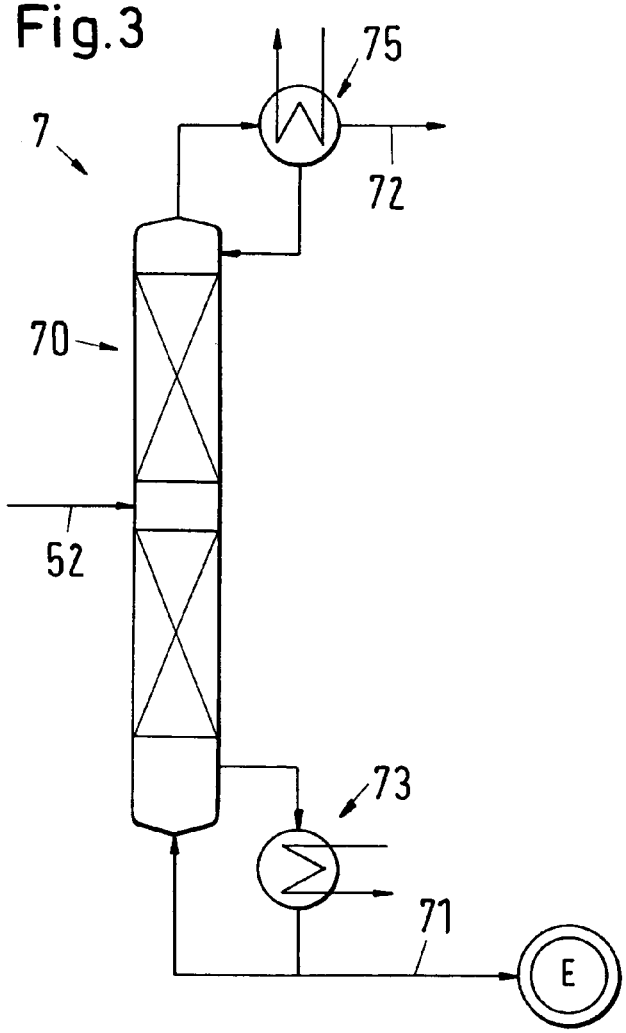
FIG. 3 illustrates a plant part for cleaning the carboxylic acid ester produced, as prescribed in the process in accordance with the invention.

The removal of acetic acid S and alcohol A from the first sump product is carried out by distillation on the packing in the second column 70 (see FIG. 3). The column is filled with material exchange means, for example bulk filled bodies, structured packings or bases. In this arrangement, heat (heating apparatus 73) is supplied to a second sump product, i.e. the sump product of the second column 70, at an overpressure compared with the environment, with the second sump product largely consisting of ester E (for example, butyl acetate or isobutyl acetate) and small amounts of further materials (for example 50 ppm acetic acid).

The operating conditions in the second column 70 are predetermined in such a way that the pressure with respect to a separation by distillation is as large as possible, namely that the absolute pressure at the lower edge of the inserts amounts to at least 1.5 bar and preferably to more than 2 bar—if possible, preferably to considerably more than 2 bar. Since an increased pressure also signifies an increased temperature, the pressure in the second column 70 is preferably limited upwardly to 3 bar due to problems with corrosion and strength.

In one embodiment, the first column 1 is operated under vacuum and the second column 70 is operated under a pressure of up to 5 bar absolute.

A second head product, i.e. the distillate of the second column 70, is subjected to liquefaction in a condenser 75 with water being recycled to the head of the column 70 and the organic phase being returned via the line 72 to the line 22 (see FIG. 1) to be fed into the first column 1 directly or indirectly via the pre-reactor 2. This can take place together with the return of organic phase 62 of the first head product.

An alternative to neutralization of the acetic acid of the first sump product has been sought and found using the solution in accordance with the invention. Nevertheless, referring to FIG. 4, it can be of advantage if a neutralization stage 9 is connected after the sump of the second column 7 with which the residues of acetic acid are removed as has already been done as the last stage in the process to be improved on. FIG. 4 shows in a block diagram a special complete plant in which all above named plant parts are amalgamated: pre-reactor 2, first column 1, second column 7 and neutralization stage 9. The second sump product of the second column 7, which still contains residual acetic acid, is neutralized with a base B. The salts C which are formed in this arrangement are removed by washing and by a phase separation from the ester E. The salt load, which cannot be completely avoided, is however considerably reduced in comparison with the known method; typically 100 to 500 times less salt is produced. The salt consumption can—expressed in mol equivalents—be reduced to less than 0.05 mol %. For example, for the production of 1162 kg/h BuOAc (or 10,000 mol/h) one only has to neutralize 0.12 kg/h acetic acid instead of 12 kg/h. The salt consumption can thus be reduced from 1.9 mol % to 0.019 mol %.

The invention thus provides a process and plant for the manufacture of carboxylic acid ester which is highly efficient and which do not require neutralization with a base.

The invention further avoids the need to dispose of a large amount of separated salts that would otherwise pollute the environment.

What is claimed:

1. A process for the manufacture of carboxylic acid ester comprising the steps of supplying alcohol and carboxylic acid to a catalytic reaction zone of a first column for esterification therein at a pressure not greater than ambient pressure to obtain a first vaporous head product at an upper end of the first column and a first liquid sump product at a lower end of the first column;

supplying heat to the tower end of the first column to effect said esterificatlon;

directing the first liquid sum product into a second column having material exchange means therein;

distilling the first liquid sump product in a reaction zone of the second column at a pressure greater than 1.5 bar to obtain a second vaporous head product containing carboxylic acid at an upper end of the second column and a second liquid sump product containing carboxylic acid ester at a lower end of the second column;

supplying heat to the second liquid sump product at said pressure greater than 1.5 bar; and removing the second liquid sump product with an a carboxylic acid content of less than 100 ppm by weight.

2. A process as set forth in claim 1 wherein the carboxylic acid ester is one of butylacetate and isobutylacetate, the alcohol is one of butanol and isobutanol and the carboxylic acid is at least one of acetic acid and acetic anhydride.

3. A process as set forth in claim 1 wherein the pressure below the material exchange means in the second column is in the range of from 1.5 to 5 bar.

4. A process as set forth in claim 1 wherein the pressure below the material exchange means in the second column is greater than 5 bar.

5. A process as set forth in claim 1 further comprising the steps of liquefying the first vaporous head product, separating the liquefied first head product into an organic phase and water, combining the organic phase with the second vaporous head product in a pre-reactor to form a mixture and supplying the mixture to the catalytic reaction zone of the first column.

6. A process as set forth in claim 1 wherein the carboxylic acid and alcohol are in a molar ratio of from 5:1 to 1:20.

7. A process as set forth in claim 1 wherein the carboxylic acid and alcohol are separately supplied to the catalytic reaction zone of the first column.

8. A process as set forth in claim 1 wherein the carboxylic acid and alcohol are supplied in a mixture to the catalytic reaction zone of the first column.

9. A process as set forth in claim 1 further comprising the steps of liquefying the first vaporous head product, separating the liquefied first head product into an organic phase and water, and combining from 60% to 100% of the organic phase with the alcohol supplied to the catalytic reaction zone of the first column in a mass ratio of organic phase to alcohol of from 5:1 to 1:20.

10. A process as set forth in claim I wherein the catalytic reaction zone of the first column includes catalyst-containing inserts providing for contact between the catalyst and a liquid phase flowing through said zone and between the liquid phase and a vapor phase flowing through said zone.

* * * * *

UNITED STATES PATENT AND TRADEMARK OFFICE
CERTIFICATE OF CORRECTION

PATENT NO.        : 7,329,774 B2
APPLICATION NO. : 11/348926
DATED             : February 12, 2008
INVENTOR(S)       : Laurent Zuber et al.

Page 1 of 1

It is certified that error appears in the above-identified patent and that said Letters Patent is hereby corrected as shown below:

Column 2
Line 3, "In" should be -- in --
Line 5, "Is" should be -- is --

Column 6
Line 66, "sum" should be -- sump --

Column 7
Line 9, "an a" should be -- a --

Signed and Sealed this

Third Day of June, 2008

JON W. DUDAS
*Director of the United States Patent and Trademark Office*